United States Patent [19]

Blankenship et al.

[11] Patent Number: 4,658,834
[45] Date of Patent: Apr. 21, 1987

[54] MEDICAL APPARATUS FOR MONITORING BODY LIQUID DISCHARGE

[75] Inventors: Larry K. Blankenship, Ramona; Bradley J. Denny, San Marcos, both of Calif.

[73] Assignee: C.R. Bard, Inc., Murray Hill, N.J.

[21] Appl. No.: 476,216

[22] Filed: Mar. 16, 1983

[51] Int. Cl.$^4$ ............................................. A61B 5/00
[52] U.S. Cl. ....................... 128/771; 604/318; 604/322; 73/290 V; 73/861.27
[58] Field of Search ................. 128/760–761, 128/765–768, 771, 660; 604/322, 324–325, 317–318, 260; 367/908; 73/290 V, 861.25–861.28, 223

[56] References Cited

U.S. PATENT DOCUMENTS

| | | | |
|---|---|---|---|
| 3,561,427 | 2/1971 | Profy .................................. | 128/771 X |
| 3,661,153 | 5/1972 | Polk et al. ........................ | 604/325 X |
| 3,693,445 | 9/1972 | Johnson ............................ | 73/290 V |
| 3,742,934 | 7/1973 | Holbrook et al. ................ | 128/771 |
| 3,754,220 | 8/1973 | Sztamler et al. ................. | 128/771 X |
| 3,769,497 | 10/1973 | Frank ............................... | 128/771 X |
| 3,929,412 | 12/1975 | Villari .............................. | 128/760 X |
| 4,129,131 | 12/1978 | Naftulin ........................... | 128/767 |
| 4,229,798 | 10/1980 | Rosie et al. ..................... | 73/290 V |
| 4,305,404 | 12/1981 | Dunn ................................ | 128/771 X |
| 4,343,316 | 8/1982 | Jespersen ........................ | 128/767 |
| 4,387,720 | 6/1983 | Miller .............................. | 128/660 |
| 4,417,585 | 11/1983 | Frank ............................... | 128/771 X |
| 4,442,700 | 4/1984 | Swoboda .......................... | 73/32 A |
| 4,448,207 | 5/1984 | Parrish ............................ | 604/322 X |
| 4,500,311 | 2/1985 | Redmond et al. .............. | 604/325 X |
| 4,532,936 | 8/1985 | Le Veen et al. ................ | 128/771 X |

FOREIGN PATENT DOCUMENTS 0998905 10/1976 Canada ............................ 128/760

2900806 7/1980 Fed. Rep. of Germany ...... 128/760

*Primary Examiner*—Kyle L. Howell
*Assistant Examiner*—Angela D. Sykes
*Attorney, Agent, or Firm*—Freilich, Hornbaker, Rosen & Fernandez

[57] ABSTRACT

A medical apparatus for automatically measuring and displaying the quantity of a liquid discharged by a patient during a defined real time interval. The apparatus is comprised of a reusable housing and a disposable plastic container adapted to be removably received in a cavity in the housing. A transducer is mounted in the floor of the cavity to engage the container and transmit sonic pulses through the container wall into a liquid pool in the container. A molded silicon rubber cap is fitted over the transducer to assure good acoustic coupling between the transducer and the container without requiring the use of an intermediate gel substance. The container is configured such that when it is received in the housing cavity, it is oriented to cause liquid entering an inlet port in the top portion to pool over the flat section of the container bottom wall. The apparatus includes an electronic measurement subsystem for measuring both the volume of liquid in the container and the passage of real time and for digitally displaying the volume of liquid accumulated within a defined real time interval. The measurement subsystem periodically samples the liquid level in the container by energizing the transducer to transmit an ultrasonic pulse. The pulse travels through the container wall and the liquid pool and is reflected off the surface of the pool. The reflected pulse then again passes through the liquid pool and is received by the transducer. The measurement unit determines the travel or "flight" time duration between pulse transmission and pulse receipt.

18 Claims, 15 Drawing Figures

MEDICAL APPARATUS FOR MONITORING BODY LIQUID DISCHARGE

BACKGROUND OF THE INVENTION

This invention relates generally to medical apparatus for monitoring the discharge of body liquids, e.g., urine.

Many devices are disclosed in the prior art for performing urine measurement. For example only, attention is directed to U.S. Pat. No. 4,343,316, and to the various references cited therein, which discloses an automatic measuring device operating on the fill and dump principle.

A preferred medical apparatus which electronically measures and displays the discharge of body liquids, such as urine, is disclosed in U.S. patent application Ser. No. 317,611 filed Nov. 3, 1981 by John H. Parrish and assigned to the same assignee as the present application.

The importance of monitoring discharged body liquids has long been known to the medical profession. For example, low urine output often gives early warning of inadequate blood flow and possible impending heart and primary renal failure. Traditionally, urine volume output of hospitalized patients has been monitored by a nurse periodically visually examining the contents of a calibrated disposable bag coupled to the patient by a catheter and flexible tubing.

More recently, automatic measuring devices, as exemplified by aforecited U.S. Pat. No. 4,343,316, have been disclosed which operate on a fill and dump principle, i.e., a small calibrated volume is repeatedly filled and dumped into a larger receptacle. A significantly different principle is employed in the aforementioned patent application Ser. Np. 317,611 which includes a disposable coontainer and an electronic measurement unit for measuring the liquid in the container and the passage of real time and for displaying the quantity of liquid accumulated in the container within a defined real time interval.

SUMMARY OF THE INVENTION

The present invention is directed to an improved medical apparatus for indicating the rate at which a liquid is discharged by a patient.

In accordance with the invention, the apparatus is comprised of a reusable housing and a disposable plastic container adapted to be removably received in a cavity in the housing. A transducer is mounted in the floor of the cavity to engage the container and transmit sonic pulses through the container wall into a liquid pool in the container.

In accordance with one aspect of the invention, means for provided to assure good acoustic coupling between the transducer and the container without requiring the use of an intermediate gel substance. In the preferred embodiment, a molded silicon rubber cap is fitted over the transducer with their smooth mating surfaces intimately contacting one another. The cap upper surface is slightly domed to enable it to make essentially single point contact with a smooth flat section of the bottom wall of the container. The cap material is selected so as to be sufficiently compliant to intimately conform to the container wall flat section and avoid any air entrapment therebetween. The cap material is also sufficiently resilient to enable it to tolerate static loads in excess of five pounds and quickly recover its shape.

In accordance with a feature of the preferred embodiment, the plastic container is configured such that when it is received in the housing cavity, it is oriented to cause liquid entering an inlet port in the top portion of the container to pool over the flat section of the container bottom wall.

In accordance with another aspect of the invention, an electronic measurement unit or subsystem is provided for measuring both the volume of liquid in the container and the passage of real time and for digitally displaying the volume of liquid accumulated within a defined real time interval. The measurement subsystem periodically samples the liquid level in the container by energizing the transducer to transmit an ultrasonic pulse. The pulse travels through the container wall and the liquid pool and is reflected off the surface of the pool. The reflected pulse then again passes through the liquid pool and is received by the transducer. The measurement unit determines the travel or "flight" time duration between pulse transmission and pulse receipt which is related to the liquid volume in the container.

In accordance with the preferred embodiment, several aspects of a patient's liquid output are monitored and displayed; e.g.,:

(1) CURRENT LIQUID VOLUME (milliliters)
(2) CURRENT INTERVAL DURATION (minutes)
(3) CURRENT INTERVAL OUTPUT (milliliters)
(4) CURRENT FLOW RATE (milliliters/hour)
(5) PRIOR INTERVAL OUTPUT (milliliters)

In accordance with an important feature of the preferred embodiment, the measurement subsystem includes noise reduction means to enhance the accuracy of measurement and avoid errors which might be introduced by, for example, perturbations in the pool surface which could be caused by the apparatus being jarred. The preferred measurement subsystem includes a microprocessor which takes multiple samples (e.g., approximately 100 samples per second) in order to develop each liquid volume reading. More particularly, the microprocessor periodically activates the transducer and after each pulse is transmitted and received, derives a flight count (or "sample") representing the time duration required for the pulse to travel from the transducer to the pool surface and back to the transducer. Each derived flight count is verified for reasonableness, as for example, by comparing it to preceeding flight counts. After a sufficient number of "good" samples are acquired, the microprocessor determines a representative flight count, and based thereon develops a reading of the current liquid volume in the container.

In accordance with a further feature of the preferred embodiment, a status indicator is provided to indicate the reliability of the displayed information. Thus, the measurement subsystem includes means for monitoring the number of "bad" samples which occur so that a "bad data" status indicator can be energized until a sufficient number of good samples are acquired to yield a "good data" status indication. The "bad data" indicator merely indicates to an attendant that the currently displayed data is unstable.

In accordance with a further feature of the preferred embodiment, the measurement subsystem continues to operate to both measure elapsed real time and retain its previously accumulated volume related data even while an attendant is draining the container, or in fact, while the container is temporarily removed from the housing, as to ambulate the patient. Subsequently, when draining is completed, or the container is replaced, and a new volume reading is developed, the previously accumulated volume related data is updated.

The measurement subsystem preferably includes means for comparing each new liquid volume reading with the prior liquid volume reading. In the event a new reading is less than the prior reading, which will occur while an attendant is draining the container, the aforementioned "bad data" status indicator will be energized. After draining is completed, a new liquid volume reading will be developed, the volume related data will be updated and the "bad data" status terminated, all without attendant intervention.

DETAILED DESCRIPTION

Figure 1:
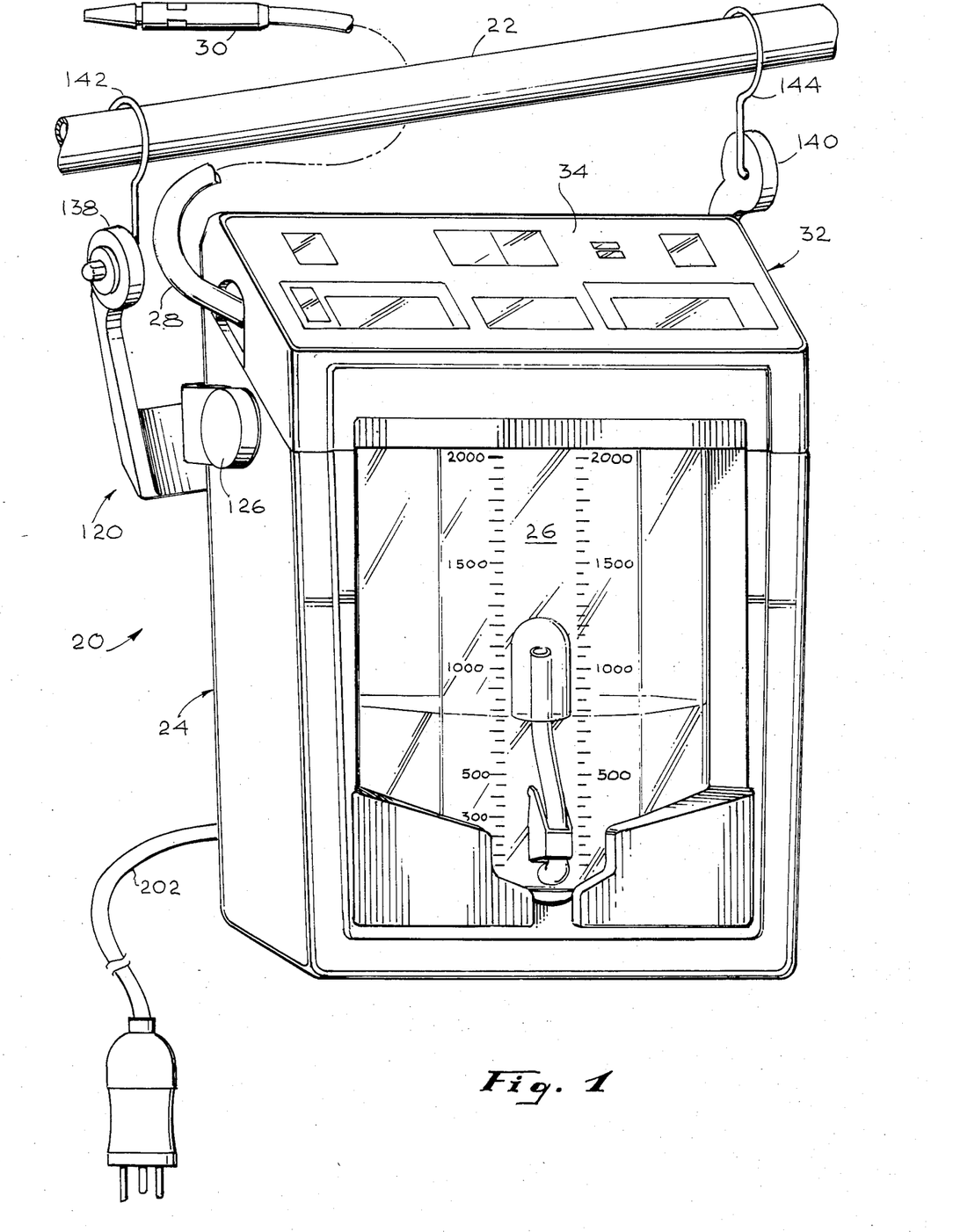
FIG. 1 is an isometric view of a medical apparatus in accordance with the present invention showing it in a typical operational situation suspended from a bedrail.

Attention is initially directed to FIG. 1 which depicts a medical apparatus 20 in accordance with the present invention suspended from a horizontally oriented bedrail 22. The apparatus 20 is comprised of a permanent reusable housing 24 and a disposable container 26 adapted to cooperate with and be supported by the housing 24. A disposable catheter tube 28 is provided having a standard catheter coupling 30 at its proximal end for communication with a catheter (not shown) connected to the patient. The distal end of the catheter tube 28 is connected to an inlet port of the container 26 to be discussed hereinafter.

Prior to describing the structural details of the embodiment depicted in the figures, it would be well for the reader to basically understand its intended application. Although an apparatus in accordance with the invention is suitable for monitoring any of various body liquids, the exemplary application to be discussed herein will assume that the apparatus is being used in a hospital situation to monitor the urine output of seriously ill patients. In such an application, the apparatus 20 is preferably suspended from a convenient location proximate to the patient, as from a rail 22 on the patient's bed or on the arm of a moveable stand located adjacent to the bed. The catheter tube 28 is connected to the patient via the catheter coupling 30 to transport urine produced by the patient to the container 26. Consistent with this application, the disposable container 26 will be assumed to have a capacity in excess of 2,000 milliliters.

The housing 24 includes a hinged lid 32 which can be opened to permit the container 26 to be readily inserted in and removed from the housing. As will be explained hereinafter, the housing 24 includes a transducer having a compliant cap positioned so as to directly engage the container wall to transmit sonic pulses therethrough and through the liquid pool accumulated in the container to the pool surface. The transducer is connected to an electronic measurement subsystem which periodically energizes the transducer and determines the travel or flight time of each sonic pulse to the pool surface and back to the transducer. Based upon a series of flight time measurements, the electronic subsystem determines the liquid volume of the pool. By also measuring elapsed real time, the electronic subsystem determines liquid flow rate and displays this and other information on a digital display panel 34 mounted in the housing lid 32.

With continuing reference to FIGS. 2–6, it is pointed out that the housing 24 is basically comprised of a body member 36 to which the lid 32 is connected by hinge 38. The hinge 38 permits the lid 32 to pivot from the closed operational position depicted in FIGS. 1 and 5 to the open position depicted in FIGS. 2 and 6.

The housing body member 36 preferably comprises a molded plastic structure including a rear member 40, a bottom cross member 42, and left and right side members 44 and 46. The side members 44 and 46 project forwardly from the rear member 40 to thus form a cavity 48 above the bottom member 42. The cavity 48 is dimensioned and shaped so as to closely receive the disposable container 26 therein in a particular orientation to be discussed hereinafter. More particularly, the upper surface of the bottom member 42, that is the floor surface of the cavity 48, is shaped to define a rear forwardly and downwardly sloping section 50. The forward portion of the cavity floor surface is comprised of side sections 52 and 54 which slope downwardly toward a substantially flat central section 56. As is shown in detail in FIG. 6A, a sonic transducer 58 is mounted in the central section 56. A silicon rubber cap 59 is fitted over the transducer 58 with the mating surfaces being smooth to permit intimate contact to achieve good acoustic coupling therebetween. The cap 59 has a domed upper surface 60 which projects slightly from the cavity floor surface 56 into the cavity 48 for engagement with the container bottom wall. The cap material is selected so as to be sufficiently compliant to enable it to intimately contact the container wall at essentially a single point so as to avoid any air entrapment therebetween. The cap material should also be sufficiently resilient to tolerate static loads in excess of five pounds with the ability to quickly recover its shape. An electrical wire 62 is connected to the transducer 58 and extends to the measurement subsystem to be discussed hereinafter.

Figure 5:
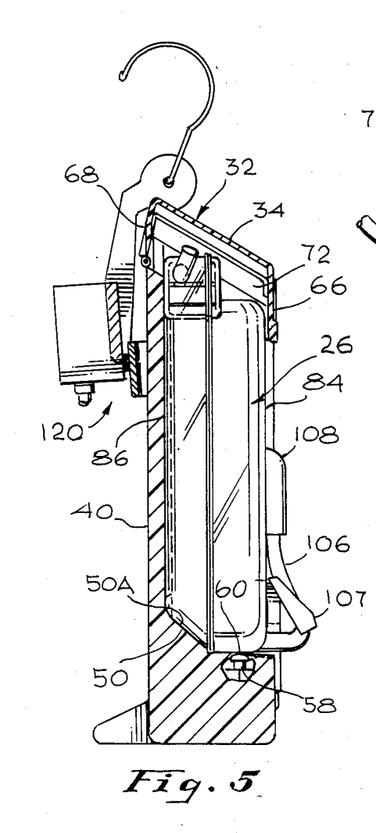
FIG. 5 is a sectional view taken substantially along the plane 5—5 of FIG. 3.
Figure 6:
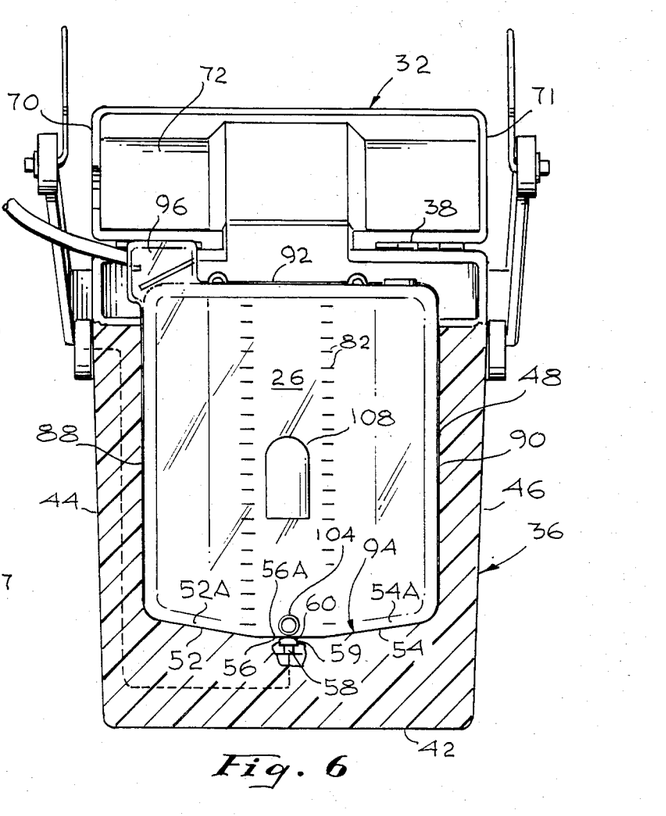
FIG. 6 is a front sectional view of the apparatus of FIG. 5 with the lid open.
Figure 6A:
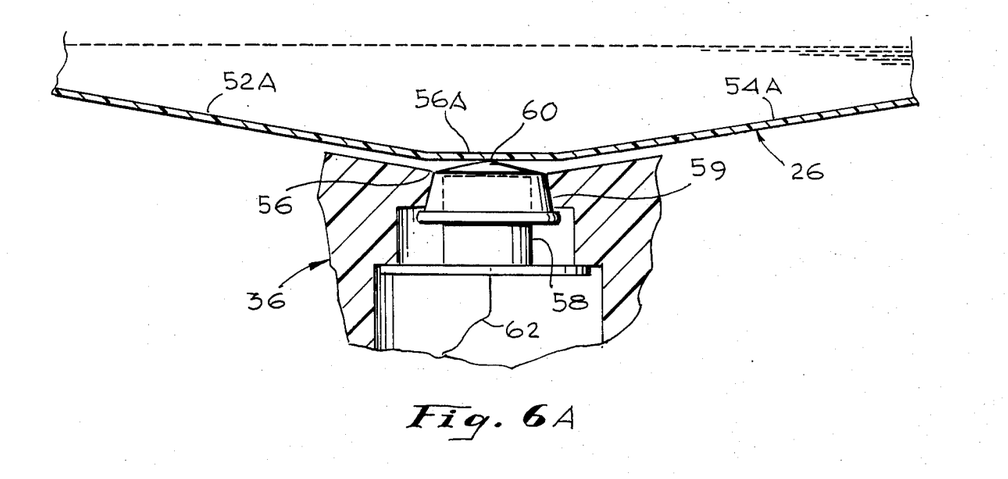
FIG. 6A is an enlarged detailed view of a portion of FIG. 6 showing the transducer/container interface.

The lid 32 is mounted to the rear member 40 of the body member 36 by hinge 38. The lid 32 defines depending front and rear walls 66 and 68 and bridging sidewalls 70, 71. Together, the walls of the lid 32 define a small cavity 72 which overlays the cavity 48 defined by the body member 36 to retain the container 26 therein as is best depicted in FIGS. 5 and 6.

Figures 9, 10:
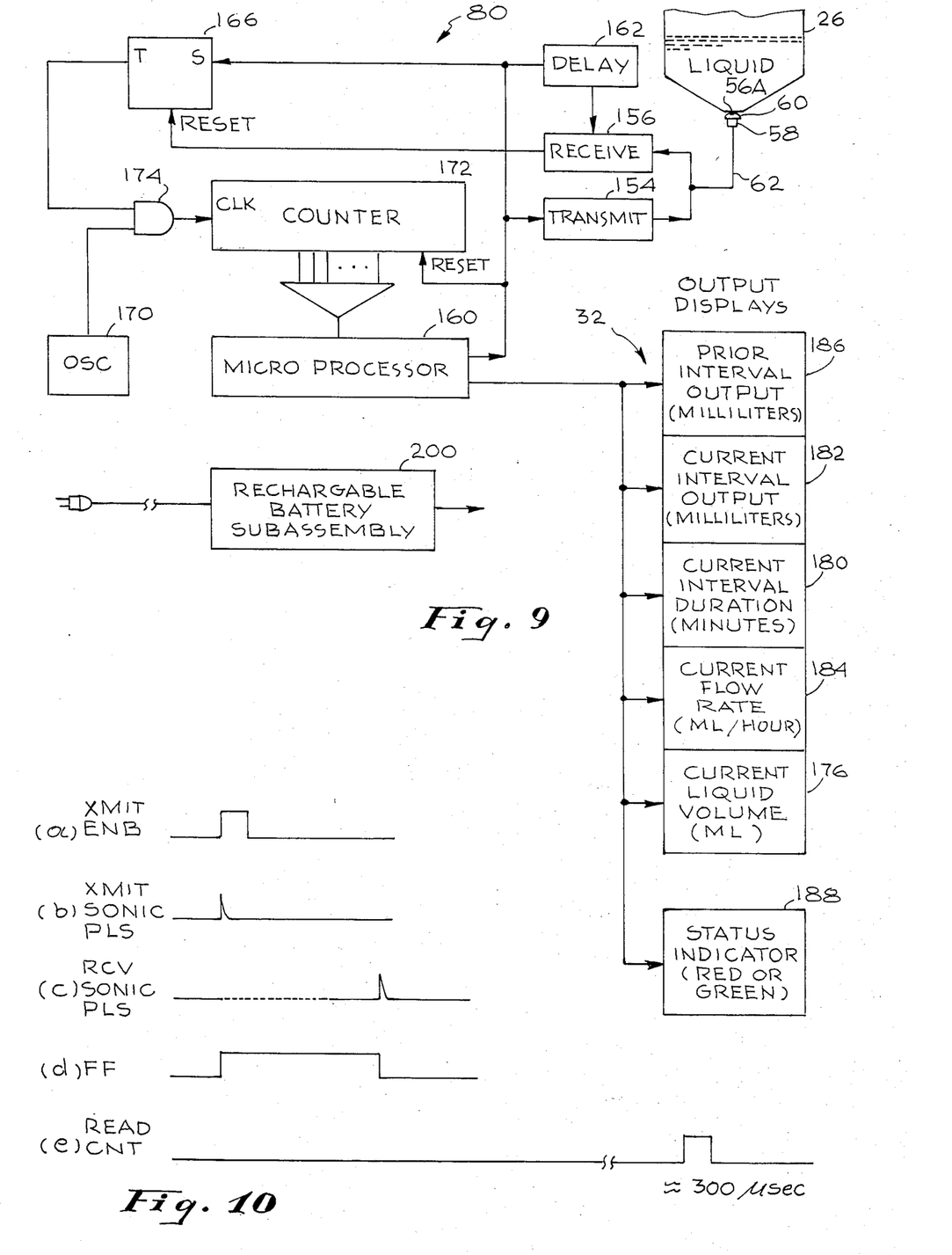
FIG. 9 is a block diagram of the electronic measurement and control subsystem incorporated within the apparatus of FIG. 1.
FIG. 10 is a timing chart depicting the pulse sequence occurring each time a sonic pulse is transmitted.

The electronic measurement subsystem 80, depicted in block diagram form in FIG. 9, is mounted within the housing 24 with the aforementioned digital display panel 34 oriented above the small cavity 72. The panel 34 is preferably sloped forwardly and downwardly to facilitate viewing when the lid is in the closed position as depicted in FIGS. 1 and 5.

Figures 2, 3, 4, 7, 8:
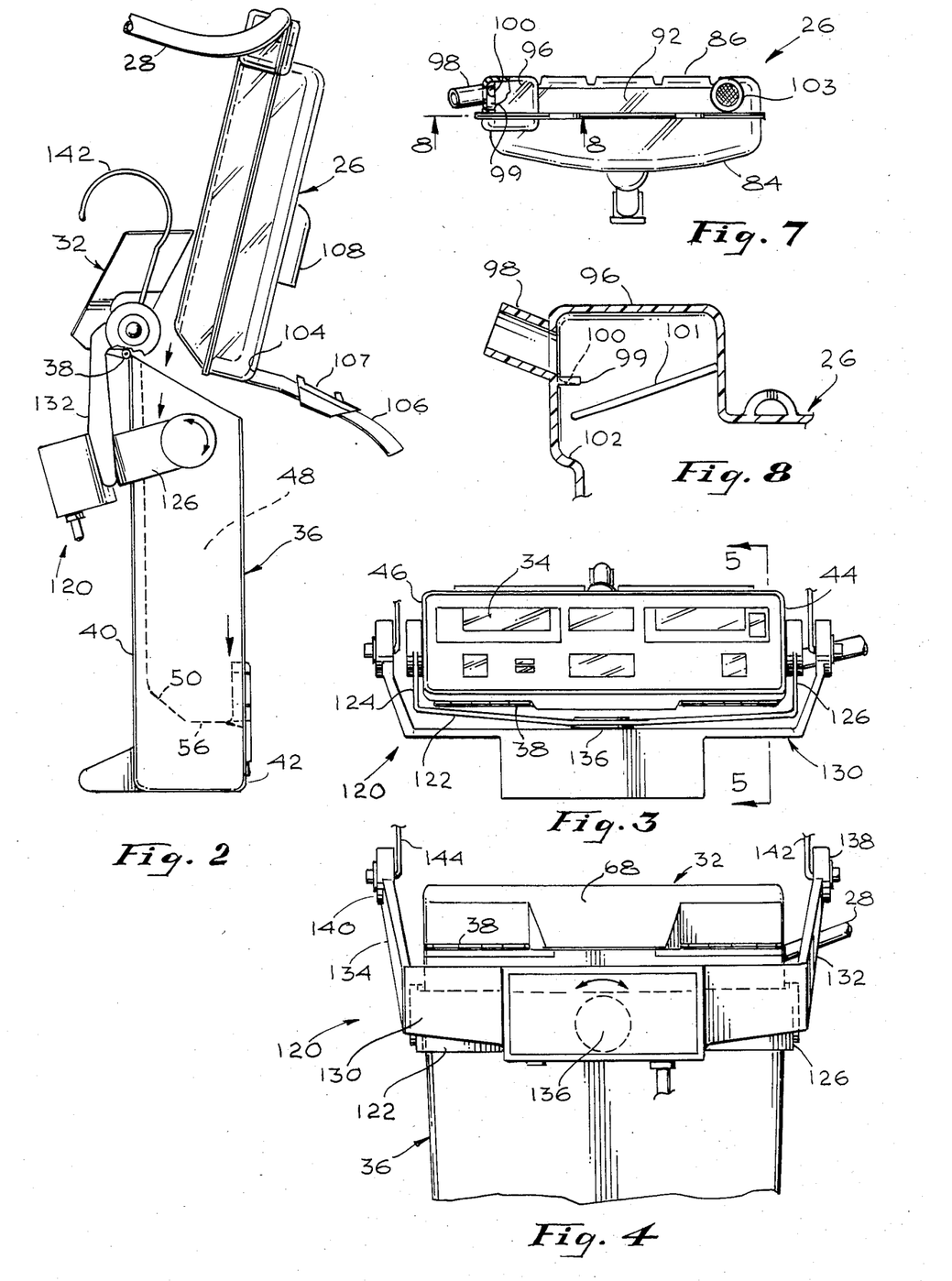
FIG. 2 is a side elevation view of the apparatus of FIG. 1 showing the manner in which a disposable container can be inserted into an removed from the reusable housing.
FIG. 3 is a top plan view of the apparatus of FIG. 1.
FIG. 4 is a rear plan view of the apparatus of FIG. 1.
FIG. 7 is a top plan view of the disposable container depicted in FIGS. 5 and 6.
FIG. 8 is an enlarged detailed view of the drip chamber portion of the disposable container of FIG. 7.

The urine collection container 26 is preferably formed of a substantially rigid plastic to define an internal volume of fixed dimensions. The container wall is preferably transparent, having milliliter graduations 82 thereon, to permit the approximate volume of liquid therein to be visually read. The container wall includes front and rear portions 84 and 86, left and right side portions 88 and 90, and top and bottom portions 92 and 94. The shape and dimensions of the container 26 are selected to substantially conform to the shape and dimensions of the cavity 48. More particularly, the bottom wall portion 94 of the container 26 is preferably shaped so as to have a rear forwardly and downwardly projecting section 50A conforming to the section 50 of the cavity floor surface. Similarly, the container bottom wall portion includes sloping side sections 52A and 54A conforming to the sections 52 and 54 of the cavity floor surface. Significantly, the container bottom wall portion includes a flat central section 56A intended to engage the domed surface 60 of transducer cap 59.

With the container bottom wall portion 94 shaped as aforedescribed sloping toward the central flat section 56A, any liquid in the container will pool over the section 56A, assuming, of course, that the housing 24 is substantially horizontally oriented. By assuring intimate single point contact of the container bottom wall portion central section 56A and the transducer cap surface 60, sonic pulses produced by the transducer 58 can be coupled directly through the wall section 56A without the necessity of using an intermediate gel substance. As will be discussed hereinafter, each sonic pulse transmitted by the transducer travels through the wall section 56A and the liquid pool and is reflected from the upper pool surface back to the transducer. The electronic measurement subsystem 80 measures the travel or flight time of each sonic pulse and based on a series of such measurements determines the volume of liquid within the fixedly dimensioned container.

As depicted in FIG. 8, the container upper wall portion 92 is formed so as to define a drip chamber 96 immediately beneath an inlet nipple 98. The inlet nipple 98 is adapted to receive thereon the distal end of the previously mentioned catheter tube 28. The drip chamber 96 includes a first shelf 99 having a flow directing dimple 100 therein and a second inclined shelf 101. The purpose of the drip chamber 96 is to prevent the formation of a continuous urine column from the pool within the container 26 to the catheter tube 28. The existence of such a continuous column could provide a bacteriological path from the urine pool to the patient. In order to prevent the formation of such a continuous column, the shelves 99 and 101 are located so as to interrupt the column and require that urine entering the inlet port 98 from the tube 28 successively fall from the shelf 99 to the shelf 101, from which it rolls off onto ledge 102 and then down the container side wall into the pool above the container bottom wall central section 56A.

The upper wall portion 92 of container 26 is vented at aperture 103 to permit air to flow out of the container as urine enters, or air to flow in as the container is drained. Preferably, a bacteriological filter (not shown) is mounted within the aperture 103.

The front wall portion 84 of the container 26 is apertured at 104 to define a drain port. A short flexible tube 106, having a clamp 107, thereon, is coupled to the drain port 104. A retainer 108 is mounted on the outside of the container front wall portion 84 to receive and retain the distal end of the tube 106 therein. In order to drain the urine from the container 26, the distal end of the tube 106 is pulled from the retainer 108, the clamp 107 is released, and the end of tube 106 is placed below the level of the drain port 104.

In order for the apparatus to most accurately measure the urine volume within the container 26, the container should be oriented vertically with the flat section 56A of the bottom wall portion extending horizontally. In order to so orient the container 26, a gimbal mechanism, best shown in FIGS. 3 and 4, is provided for supporting the housing. The gimbal mechanism includes a first U-shaped bracket 122 having first and second forwardly projecting arms 124 and 126. At their forward ends, the arms 124 and 126 are mounted for pivotal motion around spindles (not shown) extending outwardly from the side members 44 and 46 of the housing body member 36. The gimbal mechanism 120 also includes a second U-shaped bracket 130 having upwardly extending arms 132 and 134. The first and second U-shaped brackets 122 and 130 are connected to one another for relative pivotal movement about axis 136. The upwardly extending arms 132 and 134 terminate in sleeves 138 and 140. Supporting hooks 142 and 144 have ends at right angles journalled in the sleeves 138 and 140. The upper ends of the hooks 142 and 144 are arcuately shaped to enable them to hang over and suspend the housing 24 from the bar 22, as shown in FIG. 1.

With the aforedescribed gimbal arrangement, the housing 24 is able to pivot about a first horizontal axis defined by the ends of arms 124 and 126 to enable the central flat sections 56 and 56A to become horizontally oriented, front to back. Additionally, the housing can also pivot about a second horizontal axis 136 extending front to rear to enable the central flat sections 56 and 56A to assume a side to side horizontal orientation. Thus, with the bar 22 essentially horizontally oriented, the degrees of freedom permitted by the gimbal mechanism 120 will permit the housing 24, and thus container 26, to orient itself to assure a horizontal orientation of the central flat sections in both side to side and forward to rear directions. With the apparatus so oriented, the electronic measurement subsystem 80, to be described hereinafter, can accurately measure and display the volume of urine within the container. The manner in which the subsystem determines the volume of urine has previously been alluded to. Attention is now directed to the block diagram of FIG. 9 which depicts the organization of the electronic subsystem 80.

FIG. 9 schematically illustrates the container 26 with its flat central section 56A engaging the domed surface 60 of the transducer 58. The transducer 58 will be assumed to be a conventional ultrasonic transducer operating at a frequency on the order of 3.5 megahertz, although it should, of course, be understood that various other transducers operating at different frequencies are also appropriate. The transducer is preferably sealed within a silicon rubber cap 59 which, as aforenoted, has a dome shaped surface 60. When energized by a pulse supplied by wire 62, the transducer will generate a burst of ultrasonic energy which will be assumed to typically have a duration on the order of 200 nanoseconds. As is well known, a typical ultrasonic transducer 58 can operate both in a transmit mode to transmit a burst of ultrasonic energy in response to an electrical pulse supplied thereto and in a receive mode to generate an electrical pulse when it is impacted by a burst of ultrasonic energy.

The volume measuring technique used in accordance with the present invention provides for the transducer to alternately operate in the transmit mode and the receive mode. In the transmit mode, an electric pulse supplied to wire 62 by a transmit amplifier means 154 causes the transducer to produce a burst of ultrasonic energy which travels from the transducer, through the aforementioned cap 59, through the central flat section 56A of the container, and into the liquid pool within the container. The burst will travel through the liquid until it reaches the discontinuity at the liquid surface which causes some of the energy to be reflected downwardly through the liquid. This reflected energy passes through the container central flat section 56A, through the transducer cap 59 and back into the transducer 58. The ultrasonic energy impinging on the transducer causes it to produce an electric pulse on wire 62 which is amplified by a receive amplifier means 156.

In accordance with the preferred electronic subsystem 80 depicted in FIG. 9, the transmit amplifier means 154 and receive amplifier means 156 are controlled by a programmed microprocessor 160 operating in accordance with an operational sequence to be decribed hereinafter. The microprocessor 160 can comprise any one of numerous commercially available devices, such as a Mostek MK3870. At this point, suffice it to say that the microprocessor 160 periodically provides a TRANSMIT ENABLE pulse (FIG. 10, line A). The TRANSMIT ENABLE pulse is coupled to the transmit amplifier means 154 which energizes the transducer 58 to produce the burst of ultrasonic energy (FIG. 10, line B). Additionally, the TRANSMIT ENABLE pulse sets flip flop 166 (line D). When the reflected ultrasonic energy is received by the transducer 58 (line C), the receive amplifier means 156 will supply a reset pulse to flip flop 166.

The electronic subsystem 80 of FIG. 9 includes means for measuring the duration of the travel or flight time required by the ultrasonic energy to make the round trip from the transducer, to the pool surface, and back to the transducer. This flight time measurement means includes a frequency stable oscillator 170, assumed to be operating at 16.0 megahertz, and a counter 172. While the ultrasonic pulse is in flight, flip flop 166 will enable gate 174 to thereby couple the output of oscillator 170 to the clock input of counter 172. The counter 172, which is reset by each TRANSMIT ENABLE pulse supplied by microprocessor 160, will count oscillator output pulses while the flip flop 166 is in a true state to thus accummulate a count representing the duration of the flight time. Each such count accummulated by the counter 172 will sometimes hereinafter be referred to as a sample count or merely, a "sample."

As is depicted in FIG. 10, at the end of a certain interval after the generation of the TRANSMIT ENABLE pulse, e.g., 300 microseconds, the microprocessor 160 will read the counter 172. As will be discussed hereinafter, each sample so derived is subjected to a reasonableness test, as by comparing it with prior samples, to determine whether the sample is good or bad. After a certain number N of good samples are gathered, they are subjected to a smoothing operation, such as a simple mathematical averaging. The average sample count is then used to develop a liquid volume reading. The mathematical smoothing operation minimizes the effect of perturbations at the pool surface as may be caused by jarring the apparatus. After each volume reading is developed, a determination is made as to how the liquid volume is changing; e.g., increasing, which is typical of normal operation or decreasing, as is indicative of the container being drained. Based upon the nature of the change in the liquid volume, the microprocessor 160 will then perform certain tasks which will typically involve updating the values displayed on the digital display panel 34.

The display panel 34 preferably includes independent or time shared display sections respectively identified in FIG. 9 as CURRENT LIQUID VOLUME (milliliters) 176, CURRENT INTERVAL DURATION (minutes) 180, CURRENT INTERVAL OUTPUT (milliliters) 182, CURRENT FLOW RATE (milliliters/hour) 184, and PRIOR INTERVAL OUTPUT (milliliters) 186. Additionally, the display panel 34 includes two (red and green) status indication lights 188.

The microprocessor 160 measures elapsed real time and on the display 180, indicates the portion of a current interval which has elapsed; e.g., display 180 will indicate in minutes the portion of a current one hour interval which has elapsed. Display 176 will indicate the total volume of liquid (e.g., in milliliters) currently in the container. Display 182 will indicate the volume of liquid which has accummulated during the interval indicated by display 180. The display 184 will indicate the current flow rate (e.g., in milliliters per hour) i.e., the rate at which liquid is accummulating during the current interval. Display 186 will indicate the volume of liquid accummulated during an immediately prior interval.

The electronic subsystem 80 is preferably powered by a battery subassembly 200 which is continually recharged by the 110 volt line cord 202. The subassembly 200 may, for example, use gelled electrolyte lead acid type batteries which are charged from a transformer converting the line voltage to about 10 volts. This low voltage is then wire fed to power the electronic subsystem 80 including the display panel 34 and transducer 58. Utilization of a rechargeable battery subassembly in this manner enables the system to ignore any short term loss of line voltage.

Figures 11A, 11B:
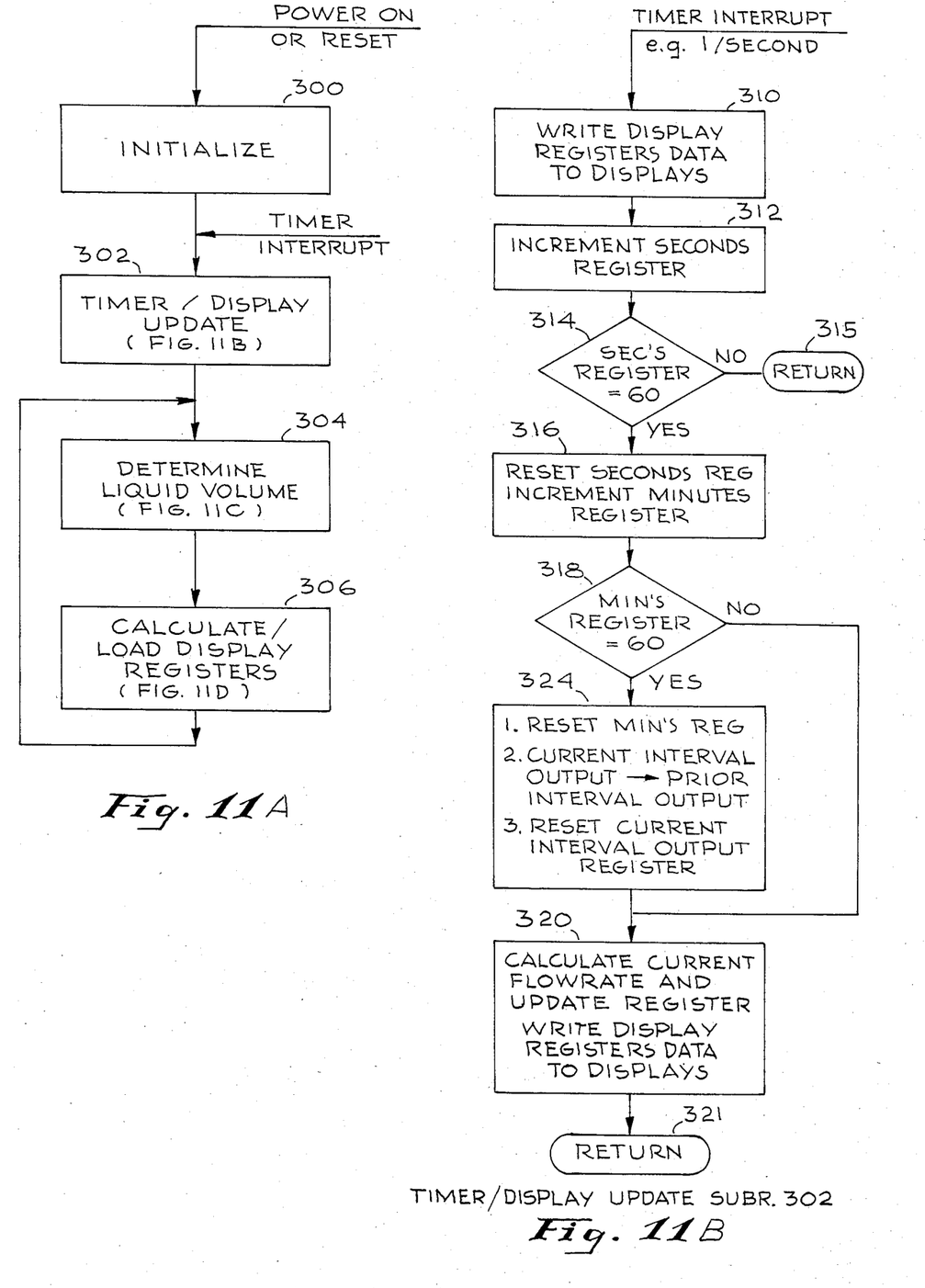
FIGS. 11A through 11D comprise flow charts describing the operation of the electronic measurement and control subsystem of FIG. 9.

Attention is now directed to FIG. 11A which comprises a flow chart generally depicting the operation of microprocessor 160. The flow chart of FIG. 11A includes a first block 300 which represents the execution of an initialize subroutine. The subroutine 300 is entered as a consequence of a POWER ON, i.e., start up condition, or by a software or hardware initiated reset.

After execution of the initialize subroutine 300, the microprocessor executes a timer/display update subroutine 302. Subroutine 302 will be discussed in greater detail in connection with FIG. 11B. Suffice it to say at this point that the subroutine 302 is executed on a periodic interrupt basis as determined by a pulse generated by a hardware timer (not shown) within microprocessor 160. The interrupt will be assumed to occur at one second intervals. During execution of the subroutine 302, the aforementioned displays 176, 180, 182, 184 and 186 are updated.

After execution of the subroutine 302, the microprocessor 160 executes the determine liquid volume subroutine 304. The details of the subroutine 304 will be discussed hereinafter in connection with FIG. 11C. It will suffice at this point to understand that during the execution of subroutine 302, the transducer will be periodically energized to acquire multiple samples or flight counts. After a sufficient number of good samples are acquired, a liquid volume reading is determined. After execution of the subroutine 304, a calculate/load display registers subroutine 306 is executed. The details of subroutine 306 will be considered in connection with Figure 11D. Basically, subroutine 306 functions to update each of a plurality of display registers. For clarity herein, it shall be assumed that the microprocessor 160 includes a different dedicated display register for each of the five displays 176, 180, 182, 184, and 186 depicted in FIG. 9. These registers can be separately implemented but in the preferred embodiment will comprise different locations in the memory of microprocessor 160. Additionally, it will also be assumed that a single bit display register is provided to define the state of the status indicator 188.

As depicted in FIG. 11A, the microprocessor will typically be executing subroutines 304 and 306 except that it will be periodically interrupted at one second intervals to execute subroutine 302.

Attention is now directed to FIG. 11B which depicts the operation of the timer/display update subroutine 302. Block 310 depicts the operational step which causes the data in the aforementioned display registers to be written into the displays 176, 180, 182, 184, 186. Thereafter, a timer register which keeps track of seconds (hence, hereinafter referred to as the seconds register) is incremented as represented by block 312. Decision block 314 then tests to determine whether the seconds register equals 60; i.e., has a full minute elapsed since the seconds register was last reset. If the test in decision block 314 yields a negative response, then the interrupt which initiate the subroutine 302 is terminated and the microprocessor 160 executes a return 315 to whatever program step it was to execute prior to the interrupt. If, on the other hand, the test defined by decision block 314 yields a positive response, then a timer register which keeps track of minutes (hence, hereinafter referred to as the minutes register) is incremented as represented by the block 316. Decision block 318 then tests to determine whether the minutes register equals 60, i.e., has one hour elapsed since the minutes register was last reset. If decision block 318 yields a negative response, then operation jumps to block 320 which causes the current flow rate to be calculated and the CURRENT FLOW RATE display register to be updated. Thereafter, as represented by block 320, the data from all of the display registers are written into their respective displays.

If the decision block 318 yields a positive response, meaning that an hour has elapsed since the minutes register was last reset, then operation steps to block 324. In block 324, the minutes register is reset to 0. The contents of the CURRENT INTERVAL OUTPUT display register is transferred to the PRIOR INTERVAL OUTPUT display register. Additionally, the CURRENT INTERVAL OUTPUT display register is reset.

After execution of the block 320, the interrupt which initiated subroutine 302 is terminated and microprocessor 160 executes a return 321 to the program step about to be performed just prior to the interrupt.

Figure 11C:
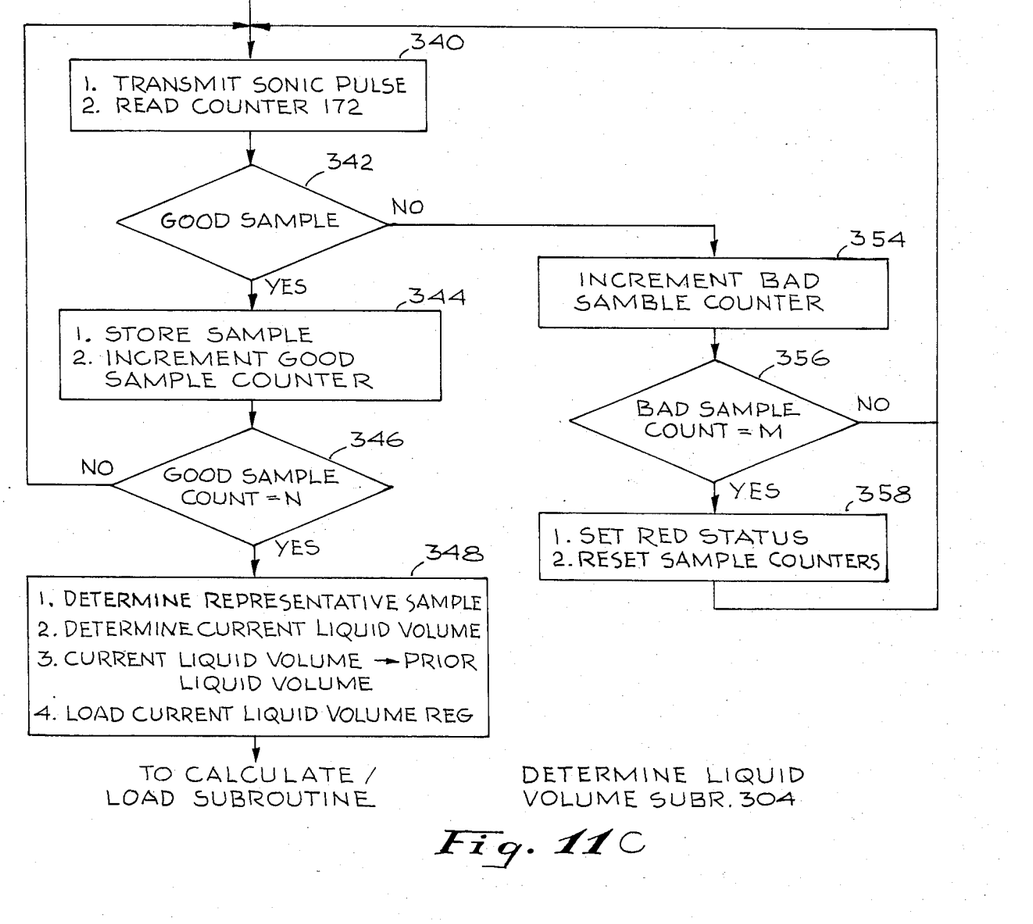

Attention is now directed to FIG. 11C which depicts the operation which occurs in aforementioned subroutine 304. Block 340 depicts the operation performed to acquire a flight count. Basically, in the execution of block 340, the sequence depicted by the aforediscussed FIG. 10 is performed. That is, a sonic pulse is transmitted from the transducer 58 to cause the counter 172 to accumulate a flight count or sample. After the sample has been acquired, decision block 342 is executed to test to see whether the sample is a good or bad sample. Prior to proceeding with a description of the steps to be executed in subroutine 304, it would assist the reader to recall the environment in which the apparatus is being used and certain factors which may effect the accuracy of acquired liquid volume readings.

As previously discussed, the apparatus in accordance with the present invention is typically used in a hospital environment in which it is suspended from a bedrail or from a support arm of a special support apparatus. In such an environment, the apparatus may be subjected to a certain amount of vibration or occasional jarring which would perturb the surface of the liquid pool in the container 26. Inasmuch as liquid volume measurements are made in accordance with the invention by reflecting an ultrasonic pulse off the pool surface, perturbations of the pool surface can give erroneous volume readings. In order to reduce the effects of such perturbations and other noise sources, the invention incorporates noise reducing means to yield more accurate volume readings.

In order to reduce the effects of surface perturbations, the invention utilizes multiple samples to derive each volume reading. Thus, a predetermined number of N good samples, e.g., 256 samples in the preferred embodiment, are taken and subjected to a smoothing operation, such as mathematical averaging, to arrive at a representative sample from which a volume reading is determined. By utilizing a large number of multiple samples to determine the volume reading, the errors that would otherwise be introduced by surface perturbations are essentially nulled.

In order to further enhance the accuracy of measurement, each derived sample is initially subjected to a test to determine whether it is good or bad. In the preferred embodiment, the good/bad test compares each newly derived sample with an appropriately weighted average of prior samples to see whether the new sample count falls within a predetermined range. If it does, then the new sample is considered a good sample and is accepted as one of the predetermined number N of samples to be used to develop a new volume reading. On the other hand, if a new sample falls outside the predetermined range, it is considered bad and not utilized in the determination of a new volume reading. Moreover, if a predetermined number M of bad samples occur prior to the occurrence of a predetermined number N of good samples, then the system discards all of the samples and starts over again to acquire new samples to determine a new volume reading.

With the foregoing background in mind, attention is again directed to FIG. 11C. Decision block 342 tests to determine whether each acquired sample is good or bad. As previously mentioned, a sample will be considered good if it has a count value which is sufficiently close to the count value of immediately preceeding samples so as to be reasonable. If the sample is good, the microprocessor 160 will exit from decision block 342 to block 344 which causes the count value of the sample to be stored and the good sample counter to be incremented. Operation then proceeds to decision block 346 which tests to determine whether the good sample counter has been incremented to a predetermined number N. That is, as has been mentioned, in the preferred embodiment it is necessary to acquire 256 good samples in order to develop a volume reading. If the test depicted by decision block 346 indicates that the good sample counter has been incremented to a count of 256, then the microprocessor steps to block 348. In block 348, the 256 good samples which have been stored are averaged to develop a representative sample or flight count. This representative sample or flight count is then used to determine the current liquid volume. It should be appreciated that inasmuch as the physical dimensions of the container 26 are fixed, a simple table look up procedure can be utilized to convert the representative sample to a liquid volume reading. Also in block 348, the contents of the CURRENT LIQUID VOLUME display register is transferred to a PRIOR LIQUID VOLUME memory register and the newly determined current liquid volume reading is loaded into the CURRENT LIQUID VOLUME display register.

If, on the other hand, decision block 346 yields a negative response, meaning that N good samples have not yet been acquired, operation jumps back to block 340.

Also, if the test depicted by decision block 342 indicates that a new sample is not a good sample, i.e., a bad sample, then operation steps to block 354 in order to increment a bad sample counter. Decision block 356 determines whether the bad sample counter has been incremented to a predetermined count M and, if so, operation steps to block 358. Block 358 causes the red status indicator to be set to indicate to a user that the displayed current data is unstable. Operation steps from block 358 back to block 340.

If the test represented by decision block 356 yields a negative response, meaning that a predetermined number M of bad samples has not yet occurred, then operation steps directly from decision block 356 back to block 340.

Figure 11D:
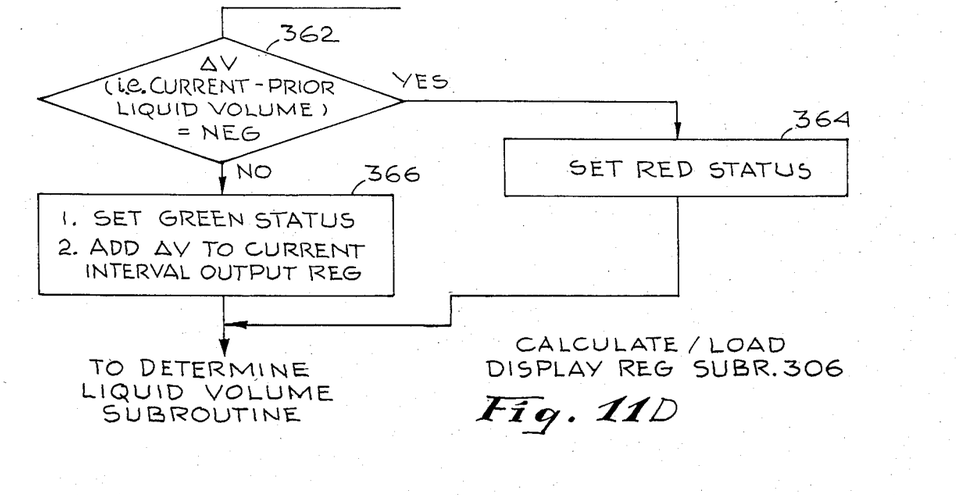

On the assumption that N good samples have been taken and that a new current liquid volume reading has been determined, operation will exit from block 348 of subroutine 304 and enter decision block 362 of the calculate/load subroutine 306, depicted in FIG. 11D.

Decision block 362 examines the change in successive volume readings. That is, the difference between the current liquid volume reading and the prior liquid volume reading ($\Delta V$) is determined. If $\Delta V$ is negative meaning that the current liquid volume reading is less than the prior liquid volume reading, this indicates that the container 26 is being drained. While draining is occurring, microprocessor 160 will exit from decision block 362 to block 364 in which the red status indicator is energized to indicate to the user that the current data being displayed is unstable.

On the other hand, in normal operation when the container 26 is not being drained (including after draining has been completed), the decision block 362 will yield a negative response meaning that the current liquid volume equals or exceeds the prior liquid volume. In this case, operation will step to block 366 in which the green status indicator is set and the quantity $\Delta V$ is added to the contents of the CURRENT INTERVAL OUTPUT register. After execution of block 364 or block 366, operation will return to subroutine 304 of FIG. 11C.

From the foregoing, it will be recognized that an improved medical apparatus has been disclosed herein for measuring and displaying the quantity of liquid discharged by a patient. The apparatus is characterized by the utilization of a disposable container of fixed dimensions which is receivable in a reusable housing. The housing includes a transducer which functions to periodically transmit an ultrasonic pulse through a dry interface through the container wall and into a liquid pool in the container. The ultrasonic pulse is reflected by the discontinuity at the surface of the liquid pool and returned to the transducer. A measurement subsystem within the housing determines the roundtrip time duration required for the ultrasonic pulse to travel from the transducer to the pool surface. Each measured time duration is examined to determine its reasonableness, i.e., whether it is good or bad. After a predetermined number of good measurements have been taken, they are used to develop a current liquid volume reading which is then used to update previously accumulated volume related data. The volume related data as well as real time interval information, is presented on a digital display.

It is important to recognize that the preferred measurement subsystem described herein continues to operate to both measures elapsed real time and retain its accummulated volume related data while the container is being drained and even when the container is temporarily removed from the housing. Thus, an attendant can drain the container or remove it from the housing to ambulate the patient without deteriorating the accuracy of the volume related data being accummulated by the apparatus which data is, of course, indicative of the patient's medical condition.

Although a preferred embodiment has been disclosed herein, it is recognized that modifications and variations will readily occur to those skilled in the art falling within the intended scope of the appended claims. Thus, for example, although the electronic subsystem disclosed herein utilizes a programmed microprocessor, it is, of course, recognized that the subsystem could alternatively be implemented utilizing dedicated hardware.

What is claimed is:

1. Medical apparatus useful for measuring the discharge of a liquid, such as urine, from a patients body, comprising:
   housing means including a cavity having a floor surface;
   a substantially rigid wall container removably receivable in said cavity with a bottom wall portion of said container supported on said floor surface;
   conduit means for supplying said discharged liquid to the interior of said container to form a pool on an interior surface of said bottom wall portion;
   transducer means mounted in said floor surface for engaging an exterior surface of said container bottom wall portion whereby said transducer means is bacteriologically isolated from the liquid in said container;
   means for periodically energizing said transducer means to transmit energy through said bottom wall portion and said pool; and
   means for determining the time duration required for said transmitted energy to travel from said transducer means to the upper surface of said pool.

2. The apparatus of claim 1 wherein said means for determining time duration comprises processor means for measuring the travel time required for said transmitted energy to travel from said transducer means to said pool surface and return to said transducer means; and wherein said processor means includes means responsive to said measured travel time for indicating the volume of liquid in said pool.

3. The apparatus of claim 2 wherein said processor means further includes means for measuring elapsed real time; and display means responsive to said processor means for displaying the volume of liquid accumulated in said pool within a defined real time interval.

4. Medical apparatus useful for measuring the discharge of a liquid, such as urine, from a patient's body, comprising:

a container of fixed dimensions formed by a wall including a bottom wall portion having interior and exterior surfaces;

an inlet port formed in said container spaced from said bottom wall portion;

a flexible tube having a distal end coupled to said container inlet port and a proximal end adapted to be coupled to said body;

housing means for removably receiving said container with said inlet port vertically above said bottom wall portion to cause liquid entering said inlet port to pool over said bottom wall portion;

said housing means including a transducer located so as to engage said bottom wall portion exterior surface when said container is received in said housing means so as to bacteriologically isolate said transducer from the liquid in said container; and processor means for energizing said transducer to transmit a pulse and for measuring the time duration required for the pulse to travel through said bottom wall portion and said liquid pool to the upper surface thereof and for determining the volume of liquid in said pool based on said measured time duration.

5. The apparatus of claim 4 wherein said housing means includes a cavity defined by spaced side members and a connecting bottom member, said cavity being shaped and dimensioned to removably receive said container in a particular orientation with said container bottom wall portion substantially adjacent said cavity connecting bottom member.

6. The apparatus of claim 4 wherein said container bottom wall portion includes a flat section and at least one side section sloped toward said flat section whereby liquid entering said inlet port will pool over said flat section.

7. The apparatus of claim 6 including means acoustically coupled to said transducer for direct single point contact with said container flat section.

8. The apparatus of claim 7 wherein said means acoustically coupled to said transducer comprises a substantially dome-shaped cap formed of compliant material for directly contacting said container flat section without entrapping air therebetween.

9. The apparatus of claim 4 including gimbal means coupled to said housing means for supporting said container with said flat section oriented essentially horizontally.

10. The apparatus of claim 4 wherein said processor means includes means for periodically energizing said transducer and means for measuring the time required for each transmitted pulse to propagate to the upper surface of said pool and return to said transducer.

11. The apparatus of claim 4 wherein said processor means further includes means for measuring elapsed real time; and display means responsive to said processor means for displaying the volume of liquid accumulated in said pool within a defined real time interval.

12. The apparatus of claim 4 wherein said transducer is energizable to transmit an ultrasonic pulse.

13. In a medical apparatus including a container for collecting a liquid such as urine discharged from a patient's body, a subsystem for measuring the volume of liquid collected in said container, said subsystem comprising:

transducer means energizable to transmit a pulse through said liquid and receive a pulse reflected from the surface of said liquid;

means for periodically energizing said transducer means to transmit a series of pulses;

means for measuring the time duration required for each pulse to travel from said transducer means through said liquid to the surface thereof and from said surface through said liquid to said transducer means;

noise reduction means for evaluating whether each time duration measurement is good or bad; and means responsive to a predetermined number of good time duration measurements for determining the volume of liquid in said container.

14. The subsystem of claim 13 including:

a status indicator means; and means responsive to a predetermined number of bad time duration measurements for energizing said status indicator means.

15. The subsystem of claim 13 wherein said means for determining the volume of liquid in said container includes means for comparing each determined liquid volume with a previously determined liquid volume; status indicator means; and means responsive to each determined liquid volume being less than the previously determined liquid volume for energizing said status indicator means.

16. The subsystem of claim 13 including means for continually measuring elapsed real time; and means responsive to said measured elapsed real time and said determination of liquid volume for displaying the volume of liquid collected in said container within a defined real time interval.

17. A disposable container for collecting a liquid discharged from a patient's body useful in a medical apparatus including an electronic subsystem for measuring the volume of liquid collected in said container, said container comprising:

a substantially rigid wall formed to define spaced front and rear wall portions and spaced top and bottom wall portions enveloping an internal volume of fixed dimensions;

an inlet nipple formed in said wall proximate to said top wall portion and adapted to receive the distal end of a catheter tube thereon;

said bottom wall portion including a central flat section, first and second side sections contiguous with and on opposite sides of said flat section, and a rear section contiguous with said flat section and said side sections, said flat section having a smooth external surface for direct contact with an ultrasonic transducer means and wherein said side and rear sections slope downwardly toward said central flat section for causing liquid entering said inlet nipple to pool over said flat section; and drip chamber means including a shelf formed in said container between said inlet nipple and said bottom wall portion for preventing the formation of a continuous liquid column from said catheter tube to said liquid pool.

18. In a medical apparatus including a container for collecting a liquid such as urine discharged from a patient's body, a subsystem for displaying data indicative of the rate said liquid is discharged by said patient, said subsystem comprising:

means for periodically deriving a sample indicative of the volume of liquid in said container;

means for comparing each newly derived sample with one or more previously derived samples to test whether or not each newly derived sample is good;

means responsive to a sequence of N good samples for developing a volume reading representing the current liquid volume in said container;

means for continually measuring elapsed real time; and means responsive to the difference between successively developed volume readings and said means for measuring elapsed real time for displaying data indicative of the rate of accummulation of liquid in said container.

* * * * *